: US005133869A

United States Patent [19]
Taniguchi et al.

[11] Patent Number: 5,133,869
[45] Date of Patent: Jul. 28, 1992

[54] CONTINUOUS HIGH PERFORMANCE LIQUID CHROMATOGRAPHY

[75] Inventors: Vernon T. Taniguchi, Anaheim; Paula J. Bosserman, Riverside; Allen W. Doty, Pomona, all of Calif.

[73] Assignee: Union Oil Company of California, Los Angeles, Calif.

[21] Appl. No.: 771,750

[22] Filed: Oct. 4, 1991

Related U.S. Application Data

[63] Continuation-in-part of Ser. No. 402,533, Aug. 31, 1989, abandoned.

[51] Int. Cl.$^5$ ............................................. B01D 15/08
[52] U.S. Cl. ................................... 210/656; 210/657; 210/659; 210/198.2
[58] Field of Search ............... 210/635, 656, 657, 659, 210/672, 673, 198.2; 55/67, 386

[56] References Cited

U.S. PATENT DOCUMENTS

| | | | |
|---|---|---|---|
| 3,062,739 | 11/1962 | Crits | 210/672 |
| 3,511,023 | 5/1970 | Saylor | 55/67 |
| 3,732,982 | 0/1973 | Dunnill et al. | 210/198 C |
| 3,865,536 | 3/1975 | James | 423/7 |
| 3,971,842 | 7/1976 | Ewbank | 423/7 |
| 4,001,112 | 1/1977 | Barker et al. | 210/31 C |
| 4,042,350 | 8/1977 | Phillips | 55/28 |
| 4,104,078 | 8/1978 | Barker et al. | 127/46 R |
| 4,172,185 | 10/1979 | Petheram | 210/673 |
| 4,276,060 | 6/1981 | Aldridge | 55/67 |
| 4,411,793 | 10/1983 | Kato et al. | 210/656 |
| 4,412,866 | 11/1983 | Schoenrock et al. | 127/46.2 |
| 4,500,430 | 2/1985 | Dasgupta | 210/638 |
| 4,528,101 | 7/1985 | Burke et al. | 210/656 |
| 4,599,175 | 0/1986 | Yamamizu et al. | 210/635 |
| 4,600,566 | 7/1986 | Fujine et al. | 423/179.5 |
| 4,849,110 | 7/1989 | Takata et al. | 210/656 |
| 4,915,843 | 4/1990 | Taniguchi | 210/659 |

FOREIGN PATENT DOCUMENTS

| | | | |
|---|---|---|---|
| 2440848 | 3/1976 | Fed. Rep. of Germany | 210/198.2 |
| 2065495 | 7/1981 | United Kingdom | 210/198.2 |

OTHER PUBLICATIONS

*Handbook on the Physics and Chemistry of Rare Earths*, Gschneider, Jr. et al. Editors, North Holland Publishing Co., New York, N.Y. (1979), pp. 81–109.
Spedding et al., *Journal of the Electrochemical Society*, 105(11): 683–686, (1958).
Spedding et al., *Journal of the American Chemical Society*, 76:2557–2560, (1954).
Snyder Introduction to Modern Liquid Chromatography, John Wiley & Sons, Inc., 1979, New York, pp. 173–184 and 238–240.
Begovich, John M., et al., "A High-Capacity Pressuzired Continuous Chromatograph," Separation Science and Technology, 18 (12 & 13), pp. 1167–1191, (1983).
Begovich, J. M., et al., "Continuous Ion Exchange Separation of Zirconium and Hafnium Using an Annular Chromatograph," *Hydrometallugy* 10 (1983), pp. 11–20.
Begovich, J. M., et al., "A Rotating Annular Chromatograph for Continuous Separations," *AICHE Journal*, (vol. 30, No. 5), Sep., 1984, pp. 705–710.
Canon, R. M. et al., "Pressurized Continuous Chromatography," *Separation Science and Technology*, 15(3), pp. 655–678 (1980).
Canon, R. M. et al., "Operation of an Improved, Continuous Annular Chromatograph," *Journal of Liquid Chromatography*, 1(4), pp. 427–441, (1978).
Chopping, G. R., et al., "Ion Exchange Studies of Alpha-Hydroxy Carboxylic Acid-Lanthanide and Actinide Systems," *Radioisotopes in the Physical Sciences and Industry; Proc. of a Conference*, vol. 3, pp. 283–299, Ion Exchange Studies (1962).

(List continued on next page.)

*Primary Examiner*—Ernest G. Therkorn
*Attorney, Agent, or Firm*—Gregory F. Wirzbicki; Shlomo R. Frieman

[57] ABSTRACT

Chromatographic species are continuously separated by either elution or displacement HPLC using an apparatus that comprises a stationary inlet distribution manifold, a stationary chromatographic bed, and mobile collector receptacles.

19 Claims, 5 Drawing Sheets

OTHER PUBLICATIONS

Cunninghame, J. G., et al., "The Rapid Separation of Rare-Earth Fission Products by Cation Exchange, using Lactic-Acid Eluant," *J. Inorg. Nucl. Chem.*, 1955, 1, pp. 163-164.

Frieling, E. C. et al., "Ion Exchange as a Separations Method. VII. Near Optimum Conditions for the Separation of Fission Product Rare Earths with Lactic Acid Eluant at 87°," *JACS*, 1954, 76, pp. 1021-1022.

Holm, L. W. et al., "Negative Chelate Complexes of Lanthanide and Actinide Elements," *J. Inorg. Nucl. Chem.*, 1961, vol. 19, pp. 251-261.

Howard, A. J. et al., "Separation of Sugars by Continuous Annular Chromatography," Issued Aug. 1987 as a thesis, prepared by ORNL ORNL/TM-10318 pp. iii--63.

Johnson, E. L. et al., "II. Column Theory," *Basic Liquid Chromatography*, pp. 15-51 (1978).

Kirk-Othmer Encyclopedia of Chemical Technology, vol. 19, Third Edition, pp. 842-847 (1982).

Korkisch, Johann, "Modern Methods for the Separation of Rarer Metal Ions," pp. 201-214 (1966).

Martin, A. J. P., "Summarizing Paper," *Chromatographic Analysis*, No. 17 (1949), pp. 332-336.

Mayer, S. W. et al., "Ion Exchange as a Separation Method. VI. Column Studies of the Relative Efficiencies of Various Complexing Agents for the Separation of Lighter Rare Earths," *JACS*, 1953, 75, pp. 5647-5649.

Nervik, W., "An Improved Method for Operating Ion-Exchange Resin Columns in Separating the Rare-Earth Elements," *J. Phys. Chem.* 1955, 59, pp. 690-695.

Powell, J. E. "The Separation of Rare Earths by Ion Exchange," vol. 1, Progress in the Science and Tech of Rare Earths, L. Eyring, ed., Pergamon Press (1964), pp. 62-83.

Powell, J. E., "Basic Principles Involved in the Macroseparation of Adjacent Rare Earths from Each Other by Means of Ion Exchange," *Chem. Eng. Prog.*, 1959, 55, pp. 101-113.

Powell, J. E. et al., "The Separation of Rare Earths by Ion Exchange" Trans. of *The Metallurgical Society of AIME*, vol. 21s5, Jun. 1959, pp. 457-463.

Powell, J. E. et al., "The Separation of Rare Earths," *J. of Chem. Ed.* vol. 37, No. 12, Dec., 1960, pp. 629-633.

Scott, C. D. et al., "Pressurized, Annular Chromatograph for Continuous Separations," *J. of Chromatography*, 126 (1976), pp. 381-400.

Powell, J.E., "Separation of Rare Earths by Ion Exchange," *The Rare Earths*, Chap. 5, (1971), pp. 55-73.

Spedding, F. H. et al., "The Stability of the Rare Earth Complexes with N-Hydroxyethylethylenediaminetriacetic Acid," *JACS*, vol. LXXVIII Jan.-Mar. 1956, pp. 34-37.

Streat, C. H. et al., "The Use of Gradient Elution in Optimizing Continuous Annular Ion Exchange Chromatography with Applications to Metal Separations," *Ion Exchange for Industry*, (1988), pp. 424-442.

Fujine et al., *Separation Science and Technology*, 17: 1545-1563 (1982-1983).

Sisson et al., "Chromatography," *Chemtech*, Aug. 1988, pp. 498-502.

VICI, Valco Instruments Co. Inc., pp. 26-29 (1987) (Product Bulletin).

Arehart et al., *Chemical Eng'g. Progress, 52(9): 353-359 (1956).*

Barker et al., *Separation Science and Technology*, 22, (8-10): 2011-2035, (1987).

Dunnill et al., *Biotechnol. & Bioeng. Symp. No. 3*, pp. 97-113, (1972).

Fox, *J. of Chromatog.*, 43:55-60, (1969).

Fox et al., *J. Chromatog.*, 43:48-54, (1960).

Giddings, *Analytical Chemistry*, 34(1):37-39, (1962).

Nicholas et al., *J. Chromatog.*, 43:61-65, (1969).

Svesson et al., *Science Tools*, 2:17-21, (1955).

Yoshisato et al., *Separation Science and Technology*, 21(8):727-753, (1986).

CONTINUOUS HIGH PERFORMANCE LIQUID CHROMATOGRAPHY

CROSS-REFERENCE TO RELATED APPLICATIONS

This application is a continuation-in-part of application Ser. No. 07/402,533, filed Aug. 31, 1989, which application is incorporated herein in its entirety by reference, now abandoned.

BACKGROUND

The present invention relates to high performance liquid chromatography (HPLC), HPLC apparatus, and systems for performing HPLC.

Since their inception, analytical and preparative HPLC have been performed on a batch basis. However, almost all large scale industrial processes are done on a continuous basis, e.g., the classical automobile assembly line. Accordingly, the batch approach to conducting HPLC has tended to impede the implementation of HPLC in potential large scale industrial applications.

SUMMARY

The present invention provides continuous HPLC methodologies and apparatus for use in continuous HPLC separations, such as continuous elution HPLC and continuous displacement HPLC. Like other continuous processes, the continuous HPLC process is readily amenable to large scale industrial applications.

In a version of the invention for conducting continuous elution or isocratic HPLC, the continuous HPLC system employs an apparatus that comprises a chromatographic column containing a chromatographic bed, means for simultaneously introducing two separate, liquid streams, usually at pressures of at least about 500 psig, through the chromatographic bed, and means for moving at least one stream with respect to the chromatographic bed so that substantially all of the bed is sequentially contacted with both streams.

One continuous elution HPLC method of this embodiment of the invention entails simultaneously introducing a feed stream and an eluent stream, at a pressure of at least about 500 psig each, proximate an entrance end of the chromatographic column. The streams are introduced in a manner so that the feed stream contacts a first portion of the chromatographic bed and the eluent stream contacts a second portion of the chromatographic bed. The feed stream comprises a chromatographic species X that interacts with the chromatographic bed. While simultaneously introducing the two streams, the portions of the chromatographic bed contacted by each stream are sequentially changed so that substantially all the chromatographic bed is sequentially contacted with the feed stream and the eluent stream. Substantially pure X is collected proximate an exit end of the chromatographic column.

In a continuous displacement HPLC version of the invention, the apparatus employed in the continuous HPLC system is modified so that the introduction means introduces at least three separate, liquid streams, generally at pressures of at least about 500 psig, through the chromatographic bed.

A continuous displacement HPLC method embodying features of the present invention simultaneously introduces a feed mixture stream, a displacer agent stream, and a barrier agent stream, at a pressure of at least about 500 psig each, proximate an entrance end of the chromatographic column. The feed mixture stream comprises a plurality of chromatographic species (for example, chromatographic species X and Y, wherein Y has a greater affinity than X for the chromatographic bed), the displacer agent stream comprises a reagent species D (wherein D removes or displaces X and Y from the chromatographic bed), and the barrier agent stream comprises a chromatographic species B (wherein B has a lesser affinity than X for the chromatographic bed). While simultaneously introducing the streams into the chromatographic bed, each stream is moved with respect to the chromatographic bed so that substantially all the chromatographic bed is sequentially contacted with the feed mixture stream, the displacer agent stream, and the barrier agent stream. Substantially pure X and substantially pure Y are each collected proximate an exit end of the chromatographic column.

DRAWINGS

The continuous HPLC methodologies and other features, aspects, and advantages of the present invention will become better understood with reference to the following description, appended claims, and accompanying drawings where:

DETAILED DESCRIPTION OF THE INVENTION

Figure 1:
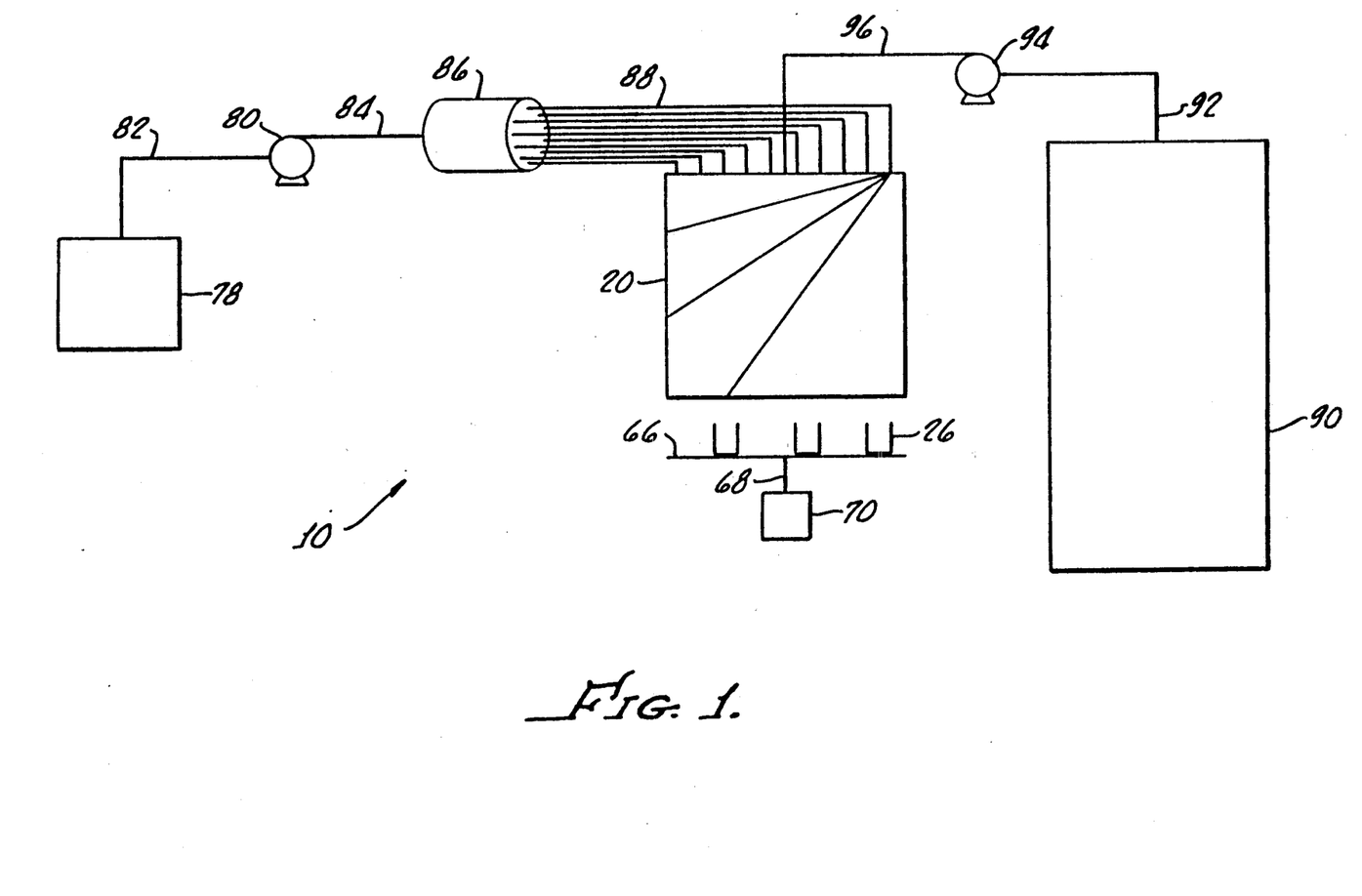
FIG. 1 is a schematic representation of a continuous, elution HPLC system embodying features of the present invention.
Figure 2:
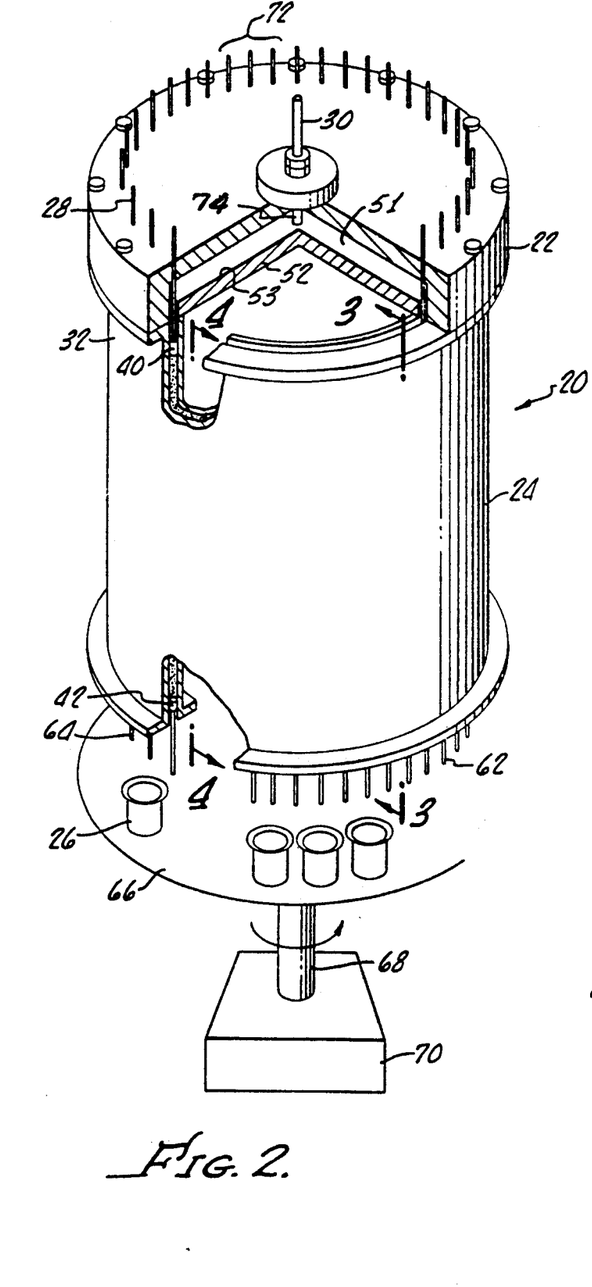
FIG. 2 is a perspective view of a continuous HPLC apparatus embodying features of the present invention.
Figure 3:
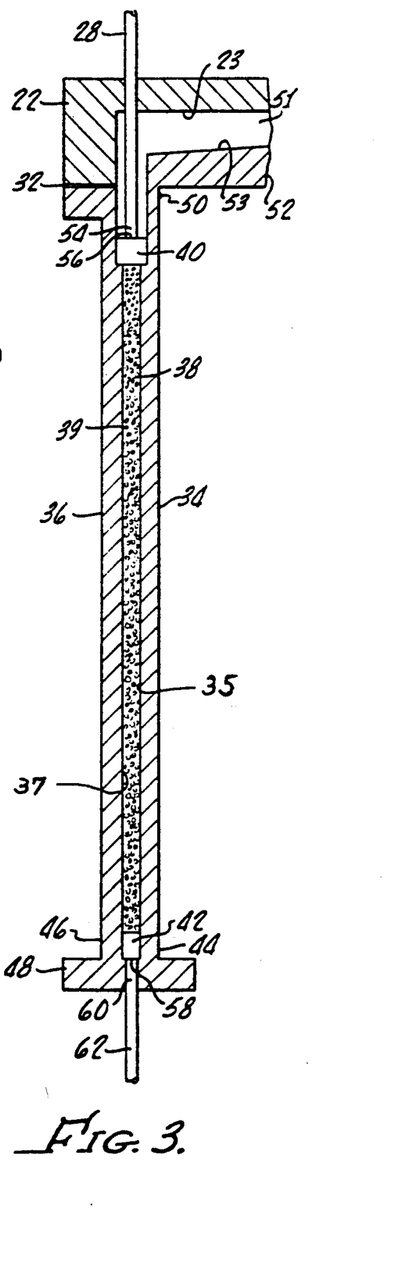
FIG. 3 is partial cross-sectional view of the continuous HPLC apparatus along lines 3—3 of FIG. 2.

With reference to FIGS. 1-3, the present invention provides an elution high performance liquid chromatography (HPLC) system 10. The elution HPLC system 10 employs a continuous HPLC apparatus 20. As best seen in FIG. 2, the apparatus 20 comprises a stationary inlet distributor manifold 22, a stationary annular column 24, and a plurality of rotating collector receptacles 26. A plurality of annularly positioned reagent inlet tubes 28 and a coaxially positioned eluent inlet tube 30 conduct fluids across the stationary inlet distributor manifold 22. The stationary inlet distributor manifold 22 is maintained in fluid tight contact with the stationary annular column 24 by means of a gasket seal 32.

The stationary annular column 24 is defined by a cylindrical inner core 34 and a coaxial cylindrical exterior shell 36. (See FIG. 3.) Sandwiched between the inner core 34 and the exterior shell 36 is a chromatographic bed 38 composed of a chromatographic material or resin 39, a porous annular distributor frit 40, and a porous annular collector frit 42. The porous annular distributor frit 40 and the porous annular collector frit 42 are porous substantially throughout their entire length and width and aid in maintaining the longitudinal integrity of the chromatographic bed 38. The radial relationship between the inner core 34 and the exterior shell 36 is maintained by permanently attaching (e.g., welding) the bottom end 44 of the inner core 34 and the bottom end 46 of the exterior shell 36 to a flange 48.

The annular thickness between the inner core 34 and the exterior shell 36 can be almost as large as the radius of the exterior shell 36. For example, the annular thickness can be such that the chromatographic bed 38 occupies up to about 95 percent of the cross-sectional area of the exterior shell 36. However, the chromatographic bed 38 typically occupies less than about 15 percent, and preferably about 1 to about 10 percent, of the cross-sectional area of the exterior shell 36. Specifically, the radial distance between the outer surface 35 of the inner core 34 and the inner surface 37 of the exterior shell 36 is usually between about 0.1 inch and about 6 feet, and more typically between about 0.2 inch to about 1 foot. However, the preferred radial distance is dependent on the anticipated output volume of material to be processed using the continuous HPLC apparatus 20. For example in low volume applications, e.g., biotechnology, the preferred radial distance is about 0.1 to about 2 inches; in moderate volume applications, e.g., pharmaceuticals, the preferred radial distance is about 1 to about 3 inches; in high volume applications, e.g., specialty chemicals, the preferred radial distance is about 2 to about 4 inches; and in very high volume applications, e.g., metals and minerals processing, the preferred radial distance is about 4 inches to about 6 feet.

The upper end 50 of the cylindrical inner core 34 forms an undetachable cover plate 52. Alternatively, the upper end 50 of the inner core 34 can he capped with a detachable cover plate (not shown) having a diameter substantially the same as the outer-diameter of the inner core 34. A cavity 51 is present between the upper surface 53 of the cover plate 52 and the lower surface 23 of the inlet distributor manifold 22.

The exit end 54 of each reagent inlet tube 28 physically contacts the upper surface 56 of the porous annular distributor frit 40. Preferably, each exit end 54 of the reagent inlet tubes 28 is in fluid tight contact with the upper surface 56 of the distributor frit 40. The lower surface 58 of the porous annular collector frit 42 is in physical contact, and preferably in fluid tight contact, with the entrance end 60 of each collector tube 62. Proximate the exit ends 64 of the collector tubes 62 are the rotating collector receptacles 26. As depicted in FIG. 2, the collector receptacles 26 sit on a carousel 66 that is rotated by a shaft 68 by means of a motor 70.

In accordance with an elution HPLC method embodying features of the instant invention, a feed stream and an eluent stream are simultaneously fed into the apparatus 10 at a pressure of at least about 500 psig each. Each stream is generally introduced at a pressure of about 500 to about 5,000 psig, and preferably at a pressure of about 800 to about 3,500 psig.

As shown in FIG. 1, the feed mixture stream originates at a feed stream source 78. The feed stream comprises a chromatographic species X that interacts with the chromatographic material 39 of the chromatographic bed 38. Typically, the feed stream comprises a plurality of chromatographic species, each of which can be separated in the annular chromatographic column 38 in substantially pure form and ultimately collected in the receptacles 26.

A feed stream pump 80 draws the feed stream from the feed stream source 78 and transports the feed stream through a conduit 82 connecting the feed stream source 78 and the feed stream pump 80. The feed stream pump 80 then pushes the feed stream through another conduit 84 that connects the feed stream pump 80 and a feed stream multiposition valve 86. Multiposition valves suitable for use in the present invention are known to those skilled in the art. See, for example, VICI by Valco Instruments, Inc., pages 26–29 (1987), the publication being incorporated herein in its entirety by reference.

Figure 4A:
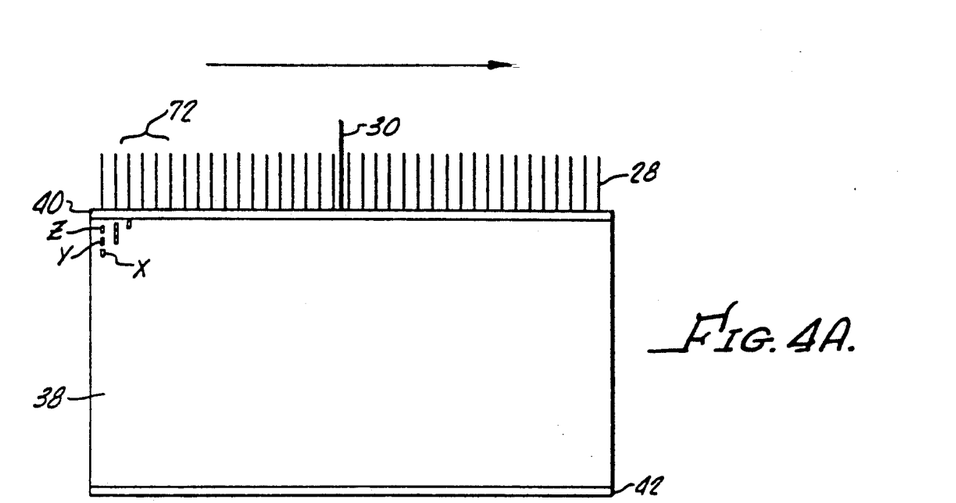
FIGS. 4A–4C are schematic, two-dimensional sectional views along lines 4—4 of FIG. 2 showing the distribution of separated chromatographic species over time in a continuous elution HPLC method embodying features of the present invention.
Figure 4B:
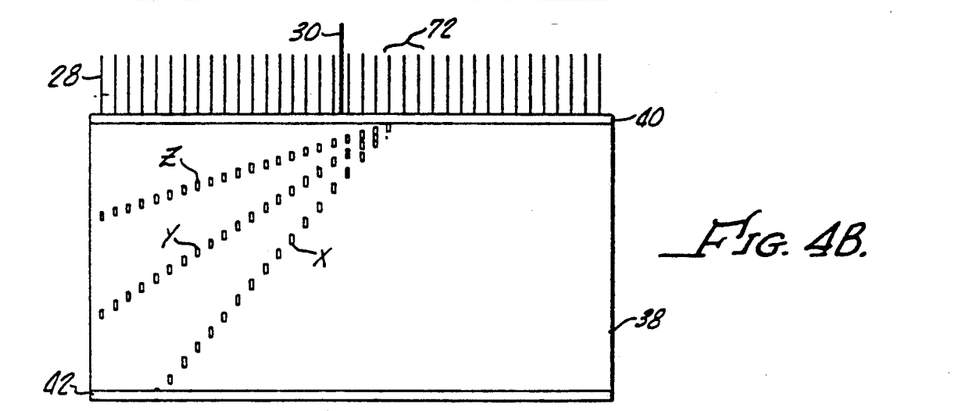
Figure 4C:
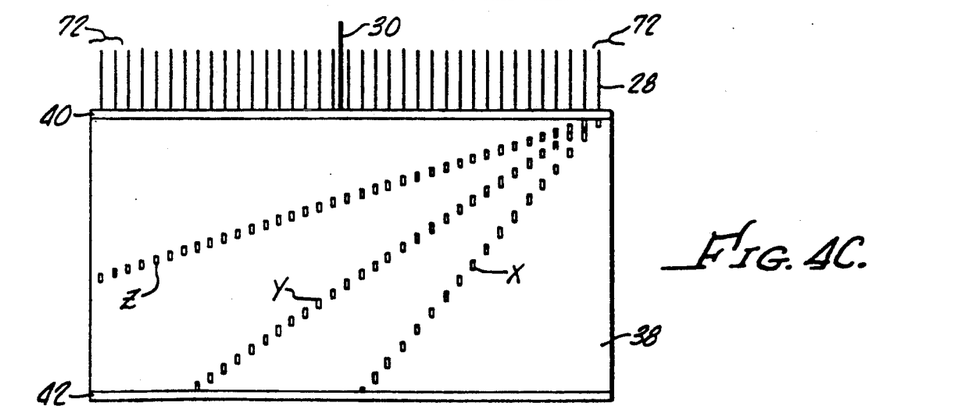

The feed stream multiposition valve 86 distributes the feed stream in a predetermined manner through feedlines 88 to a select portion or group 72 of the reagent inlet tubes 28 (as best shown in FIGS. 4A–4C). The feed stream multiposition valve 86 is adjusted so that (a) the portion 72 of the reagent inlet tubes 28 introducing the feed stream into the chromatographic bed 38 remains fixed in number and (b) this portion 72 advances continuously in a counter-clockwise manner indicated in FIG. 2 (or from left to right as displayed in FIGS. 4A–4D) with respect to the bed 38 so that substantially all the chromatographic bed 38 is sequentially contacted with the feed stream.

As best shown in FIG. 1, the eluent stream is stored in an eluent source 90. The eluent stream leaves the eluent source 90 via conduit 92 and is moved by eluent pump 94 through eluent delivery line 96 to the eluent inlet tube 30.

With reference to FIGS. 2 and 3, the feed stream exits the inlet distributor manifold 22 through the exit end 54 of the select portion 72 of the reagent inlet tubes 28. The eluent stream simultaneously exits the inlet distributor manifold 22 through the exit end 74 of the eluent inlet tube 30, fills the cavity 51 between the upper surface 53 of the cover plate 52 and the lower surface 23 of the distributor manifold 22, and radially flows, substantially equally in all directions, through the cavity 51. The eluent stream then enters the chromatographic bed 38 through the porous annular distributor frit 40 at substantially all locations except where the feed stream traverses the annular distributor frit 40. The eluent stream remains substantially distinct from the feed stream as it passes through the porous annular distributor frit 40. Although the chromatographic species introduced into the chromatographic bed 38 interact with the eluent stream, the eluent stream and the carrier fluid portion of the feed stream remain substantially distinct as these two streams traverse the chromatographic bed 38. To prevent any disruption in the steady state nature of the continuous HPLC method of the present invention, it is generally preferred that all streams be introduced through the stationary inlet distributor manifold 22 at substantially the same pressure.

Depending upon the partitioning of the chromatographic species between the eluent or mobile phase and the chromatographic bed or stationary phase 38, each species present in the feed stream is separated. For example, as schematically shown in FIGS. 4A–4C with respect to a feed stream containing three chromatographic species X, Y, and Z, as the feed stream advances from left to right, each chromatographic species is resolved into separate, substantially pure streams of X, Y, and Z. Each of the separated chromatographic species is collected in substantially pure form in one or more of the receptacles 26 (shown in FIGS. 1 and 2) which are rotated by the programmed carousel 66 with respect to the stationary annular column 24 at substantially the same annular velocity at which the feed stream multiposition valve 86 advances the feed stream with respect to the stationary annular column 24.

The elution HPLC method of the present invention can be used for both preparative and analytical procedures.

Figure 4D:
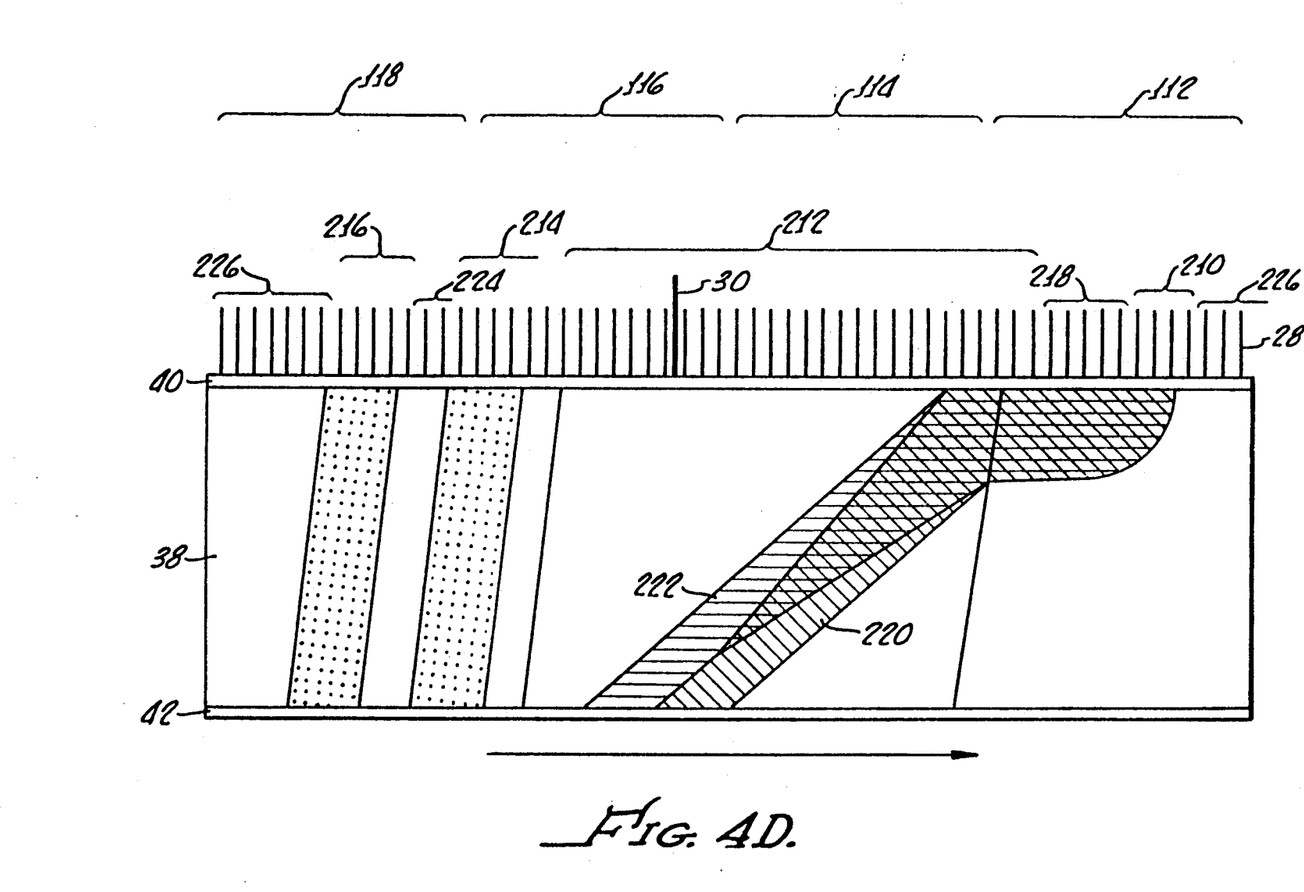
FIG. 4D is a schematic, two-dimensional sectional view along lines 4—4 of FIG. 2 showing the distribution of various reagent sectors in a continuous displacement HPLC method embodying features of the present invention.
Figure 5:
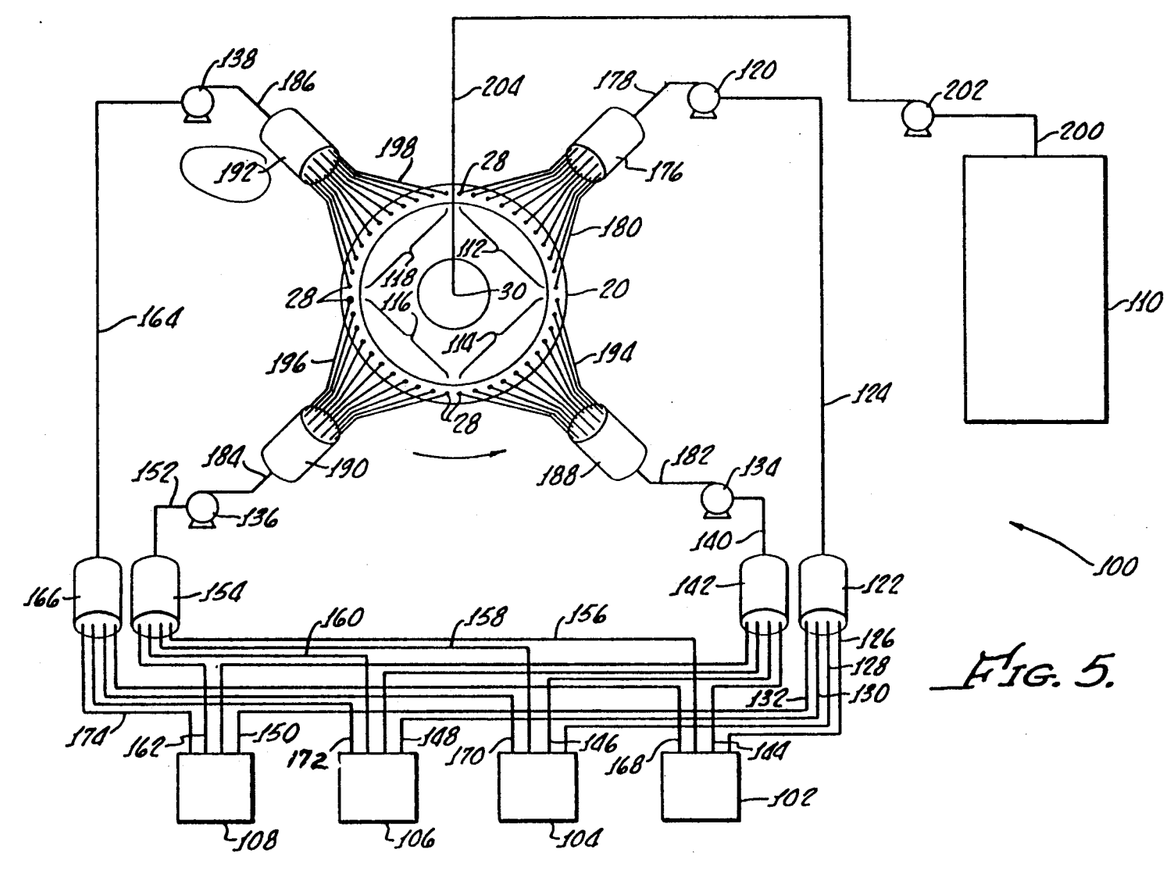
FIG. 5 is a schematic representation of a continuous, displacement HPLC system embodying features of the present invention.

In another method embodying features of the instant invention, the continuous HPLC apparatus 20 is employed in a continuous displacement HPLC system 100 schematically represented in FIG. 5 to separate a plurality of chromatographic species as schematically illustrated in FIG. 4D. As shown in FIG. 5, the continuous displacement HPLC system 100 comprises the continuous HPLC apparatus 20, a feed mixture stream source 102, a displacer reagent stream source 104, a regenerator reagent stream source 106, a barrier reagent stream source 108, and a mobile phase or eluent or purge reagent stream source 110. The reagent inlet tubes 28 are sectioned into four quadrants 112, 114, 116, and 118.

A first quadrant pump 120 is in fluid communication with the feed mixture stream source 102, the displacer reagent stream source 104, the regenerator reagent stream source 106, and the barrier reagent stream source 108. In particular, the first quadrant pump 120 is connected to a first quadrant intake multiposition valve 122 by a conduit 124. The first quadrant intake multiposition valve 122 is in fluid communication with the feed mixture stream source 102, the displacer reagent stream source 104, the regenerator reagent stream source 106, and the barrier reagent stream source 108 by conduits 126, 128, 130, and 132, respectively.

In an analogous fashion, a second quadrant pump 134, a third quadrant pump 136, and a fourth quadrant pump 138 are in fluid communication with the feed mixture stream source 102, the displacer reagent stream source 104, the regenerator reagent stream source 106, and the barrier reagent stream source 108. Specifically, the second quadrant pump 134 is connected by a conduit 140 to a second quadrant intake multiposition valve 142 that is in fluid communication with the feed mixture stream source 102, the displacer reagent stream source 104, the regenerator reagent stream source 106, and the barrier reagent stream source 108 by conduits 144, 146, 148, and 150, respectively. The third quadrant pump 136 is connected by a conduit 152 to a third quadrant intake multiposition valve 154 that is in fluid communication with the feed mixture stream source 102, the displacer reagent stream source 104, the regenerator reagent stream source 106, and the barrier reagent stream source 108 by conduits 156, 158, 160, and 162, respectively. Similarly, the fourth quadrant pump 138 is connected by a conduit 164 to a third quadrant intake multiposition valve 166 that is in fluid communication with the feed mixture stream source 102, the displacer reagent stream source 104, the regenerator reagent stream source 106, and the barrier reagent stream source 108 by conduits 168, 170, 172, and 174, respectively.

The first, second, third, and fourth quadrant pumps 120, 134, 136, and 138, respectively, are also in fluid communication with the continuous HPLC apparatus 20. In particular, the first quadrant pump 120 is connected to a first quadrant distributor multiposition valve 176 by a conduit 178. The first quadrant distributor multiposition valve is in turn connected to the reagent inlet tubes 28 in the first quadrant 112 via a plurality of first quadrant distributor conduits 180. Similarly, the second, third, and fourth quadrant pumps 134, 136, and 136 are connected by conduits 182, 184, and 186, respectively, to their respective second, third, and fourth quadrant distributor multiposition valves 188, 190, and 192. The second, third, and fourth quadrant distributor multiposition valves 188, 190, and 192 are, in turn, connected to the reagent inlet tubes 28 in their respective second, third, and fourth quadrants 114, 116, and 118 by a plurality of second, third, and fourth quadrant distributor conduits 194, 196, and 198, respectively.

The purge source 110 is in fluid communication with the continuous HPLC apparatus 20 via a conduit 200 that connects the purge source 110 with a purge pump 202. The purge pump 202 is connected to the eluent or purge inlet tube 30 of the HPLC apparatus 20 by a purge distributor conduit 204.

Generally, in the continuous displacement HPLC methods the chromatographic material or resin 39 of the chromatographic bed 38 (as illustrated in FIG. 3) is initially loaded with chromatographic barrier species B. For example, the chromatographic barrier species B can be loaded onto the resin 39 prior to the resin 39 being placed in the annular column 24. However, it is preferred to load the chromatographic species B onto the resin 39 by first passing only the barrier reagent stream through substantially all of the reagent inlet tubes 28 and through the chromatographic bed 38 until substantially all of the binding capacity of the bed 38 is occupied by chromatographic species B.

As schematically shown in FIGS. 4D and 5, the feed mixture stream, the displacer reagent stream, the regenerator reagent stream, and the barrier reagent stream are then moved by the first, second, third, and fourth quadrant pumps 120, 134, 136, and 138 in a predetermined progression through each pump's respective first, second, third, and fourth quadrant intake multiposition valves 122, 142, 154, and 166, respectively, as well as through each pump's respective first, second, third, and fourth quadrant distributor multiposition valves 176, 188, 190, and 192. The intake and distributor multiposition valves are synchronized or programmed so that each stream enters the annular column 20 through a substantially discrete, substantially separate, and substantially continuous grouping of reagent inlet tubes 28, namely, distinct groupings of the reagent inlet tubes 28 form a feed stream grouping 210 that introduces the feed stream into the HPLC apparatus 20, a displacer stream grouping 212 that introduces the displacer stream into the HPLC apparatus 20, a regenerator grouping 214 that introduces the regenerator stream into the HPLC apparatus 20, and a barrier grouping 216 that introduces the barrier stream into the HPLC apparatus 20.

The synchronized first, second, third, and fourth quadrant intake multiposition valves 122, 142, 154, and 166 and the synchronized first, second, third, and fourth quadrant distributor multiposition valves 176, 188, 190, and 192 are further programmed so that the introduction of the feed mixture stream, the displacer reagent stream, the regenerator reagent stream, and the barrier reagent stream into the chromatographic bed 38 through their respective grouping 210, 212, 214, or 216 of reagent inlet tubes 28 is sequentially advanced from left to right as shown in FIG. 4D (or counter-clockwise as correspondingly illustrated in FIG. 5).

Accordingly, chromatographic species B is displaced from the bed 38 by chromatographic species X and Y in the feed mixture stream. The feed mixture stream is introduced into the annular column 24 over a sector that generally spans at least about 5° (or at least about 1 percent of the horizontal cross-sectional area of the chromatographic bed 38). More typically, the feed mixture stream is introduced over a sector of about 10° to about 20° (or about 3 to about 6 percent of the horizontal cross-sectional area of the chromatographic bed 38).

Generally, in the continuous displacement HPLC embodiments of the invention, sufficient feed mixture stream is introduced into the bed 38 so that up to about 50 percent of the total capacity of the bed 38 is occupied by the chromatographic species X and Y. Typically, at least about 5 percent of the total capacity of the bed 38 is occupied by the chromatographic species X and Y. Since the amount of chromatographic species capable of being separated is directly proportional to the total binding capacity of the bed 38, it is preferred that the chromatographic species to be separated occupy as much of the binding capacity of the bed 38 as is consistent with displacement chromatography principles. For example, it is preferred that the chromatographic species occupy at least about 40 percent, and more preferably at least about 45 percent of the binding capacity of the bed 38.

In order to remove substantially all chromatographic species displaced by the feed mixture stream, e.g., displaced chromatographic species B, it is also preferred, as shown in FIG. 4D, that a branch of the purge stream emanating from the purge inlet tube 30 be introduced into the bed 38 in the area 218 between the feed stream grouping 210 and the displacer stream grouping 212 of the reagent inlet tubes 28.

In one version of the continuous displacement HPLC embodiment of the invention, the displacer reagent stream contains reagent species D having a greater affinity than chromatographic species X and Y for the chromatographic bed 38. Therefore, reagent species D displaces chromatographic species X and Y from the bed 38. Due to their differing chromatographic affinities for the bed 38, chromatographic species Y displaces chromatographic species X as they traverse the bed 38. In addition, chromatographic species X and Y form distinct, adjacent bands 220 and 222 containing substantially pure X and Y, respectively. The chromatographic species X and Y substantially separately pass through their adjacent, respective collector tubes 62 and are substantially separately collected at the exit end 64 of collector tubes 62 in separate, rotating collector receptacles 26 as shown in FIG. 2.

In another version of the continuous HPLC embodiment of the invention, the displacer reagent stream contains reagent species D having a greater affinity than the chromatographic bed 38 for species X and Y. Therefore, reagent species D removes chromatographic species X and Y from the bed 38. The order that X and Y leave the bed 38 depends on the affinity of the reagent species D for species X and Y as well as the affinities of X and Y for the bed 38. When species X and Y have the same affinities for the bed 38, the order that X and Y exit the bed 38 depends on the relative affinity of reagent species D for X and Y. If D has a greater affinity for X, X leaves the bed 38 first, and in the case where D has a greater affinity for Y, Y exits the bed 38 first. In cases where X and Y have different affinities for the bed 38, the order that X and Y traverse the bed 38 depends on both the affinities of X and Y for the bed 38 and the relative affinities of D for X and Y. In any event, chromatographic species X and Y form distinct, adjacent bands (not shown) containing substantially pure X and Y, respectively. The chromatographic species X and Y substantially separately pass through their adjacent, respective collector tubes 62 and are substantially separately collected at the exit end 64 of collector tubes 62 in separate, rotating collector receptacles 26 as shown in FIG. 2.

In both of the above reagent D embodiments, to substantially, fully separate species X from species Y, the reagent D is preferably introduced into the annular chromatographic column 24 over a sector having a horizontal length at least as long as the minimum critical fixed batch column length (i.e., "band length" in batch displacement chromatography terms) necessary to resolve species X from Y. The band length is the length of a fixed batch column initially occupied by the feed mixture prior to introducing the reagent D into the batch column. Typically, the reagent species D is introduced into the column 24 over a sector of at least about 100° (or at least about 33 percent of the horizontal cross-sectional area of the chromatographic bed 38). Preferably, the stream sector for reagent D is as large as possible in order to separate the maximum amount of chromatographic species per cycle. In particular, it is desirable to introduce the reagent species D over a sector that spans at least about 180° (or at least about 50 percent of the horizontal cross-sectional area of the chromatographic bed 38).

Referring back to FIG. 4D, when the reagent species D has a greater affinity for the bed 38 than X and Y, the reagent species D is removed from the bed 38 by the regenerator stream emanating from the regenerator grouping 214 of the reagent inlet tubes 28. However, when the reagent D has a greater affinity for X and Y than the bed 38, a species Z generally having a lesser affinity for the bed 38 than X and Y typically occupies the bed site vacated by X or Y. In this latter version, the species Z is also removed from the bed 38 by the regenerator stream emanating from the regenerator grouping 214 of the reagent inlet tubes 28.

The regenerator stream is usually introduced into the annular column 24 over a sector of at least about 35° (or at least about 10 percent of the horizontal cross-sectional area of the chromatographic bed 38). More typically, the regenerator stream 140 is introduced over a sector of about 35° to about 100° (or about 10 to about 30 percent of the horizontal cross-sectional area of the chromatographic bed 38).

The regenerator stream is in turn removed from the bed 38 by another branch of the purge stream entering the bed 38 along the area 224 between the regenerator grouping 214 and the barrier grouping 216 of reagent inlet tubes 28. Chromatographic barrier species B is then reloaded onto the bed 38 by the barrier reagent stream emanating from the barrier grouping 216 of the reagent inlet tubes 28. The barrier reagent stream is also usually introduced into the annular column 24 over a sector of at least about 35° (at least about 10 percent of the horizontal cross-sectional area of the chromatographic bed 38). However, the barrier reagent stream is more typically introduced over a sector of about 35° to about 100° (or about 10 to about 30 percent of the horizontal cross-sectional area of the chromatographic bed 38). Any unbound chromatographic species B is removed from the bed 38 by a further branch of the purge stream entering the bed 38 along the area 226 between the barrier grouping 216 and the feed stream grouping 210 of reagent inlet tubes 28.

After removing any excess chromatographic species B, the chromatographic bed 38 is substantially regenerated and in substantially the same condition as it was at the beginning of the cycle. The cycle can be repeated as many times as necessary and, therefore, the process is continuous. Typically, the cycle is repeated at least twice.

Although it is preferred that the feed mixture stream and each reagent stream be separated from its neighboring reagent stream or feed mixture stream by the purge stream, satisfactory results are also obtainable when various neighboring streams are not separated by the purge stream. In addition, the barrier and reagent streams occasionally act in the same manner and, in these instances, are combinable into a single reagent stream.

Any elution or displacement chromatographic method capable of being performed by a batch HPLC process can now be performed by one of the continuous HPLC methods of the present invention. Exemplary chromatographic methods include liquid-liquid, liquid-solid, ion-exchange, size-exclusion, bonded-phase, and ion-pair chromatography methods. In addition, any organic or inorganic compounds capable of being separated by a batch HPLC chromatographic method can now be separated by one of the continuous HPLC methods of the present invention. As used in the specification and claims the term "organic compound" means any compound containing at least one carbon atom, and the term "inorganic compound" means any compound devoid of even one carbon atom. Exemplary organic compounds that can be separated by the continuous methods of the present invention include, but are not limited to, drugs, proteins, antibodies, enzymes, and organometallic compounds. Exemplary inorganic compounds that can be separated by the continuous methods of the present invention include, but are not limited to, transition metals, lanthanides, actinides, and minerals.

Although the present invention has been described in considerable detail with reference to several preferred versions, other versions are possible. For example, the particulate bed, in addition to being annular, can also be linear. In addition, instead of employing multiposition valves, programmable control valves can be used to direct the flow of the various streams. Also, the sequential advancement of the feed mixture stream, the displacer reagent stream, the regenerator each stream, and the barrier reagent stream can be programmed to proceed at a variable speeds, provided that the carousel is similarly programmed to mimic the changing conditions.

Furthermore, the feed mixture stream, the displacer reagent stream, the regenerator stream, and the barrier reagent stream can be introduced into the column via separate, dedicated pumps that deliver their respective reagent to a plurality of dedicated reagent inlet tubes. In this alternative embodiment of the invention, the streams are continuously introduced into an uninterrupted portion of their dedicated reagent inlet tubes. All the uninterrupted stream portions are simultaneously rotated clockwise or counter-clockwise (or to the left or to the right) so that they uniformly advance and permit each stream to occupy a continuous segment of the chromatographic bed.

In view of the above other versions, the spirit and scope of the appended claims should not necessarily be limited to the description of the preferred versions contained herein.

What is claimed is:

1. A continuous high performance liquid chromatographic (HPLC) method comprising the steps of:
   (a) simultaneously introducing a feed stream and an eluent stream, at a pressure of at least about 500 psig each, proximate the entrance end of a chromatographic bed, so that a first portion of the chromatographic bed is contacted by the feed stream and a second portion of the chromatographic bed is contacted by the eluent stream, the feed stream comprising a chromatographic species X that interacts with the chromatographic bed;
   (b) changing the portions of the chromatographic bed contacted by the feed stream and the eluent stream; and
   (c) collecting substantially pure X proximate the exit end of the chromatographic bed.

2. The method of claim 1 wherein step (b) is repeated as many times as necessary so that all portions of the chromatographic bed are sequentially contacted by the feed and eluent streams.

3. The method of claim 1 wherein step (a) includes the step of introducing the feed stream and the eluent stream at a pressure of about 500 to about 5,000 psig each.

4. The method of claim 1 wherein step (a) includes the step of introducing the feed stream and the eluent stream at a pressure of about 800 to about 5,000 psig each.

5. The method of claim 1 wherein step (a) includes the step of introducing the feed stream and the eluent stream at a pressure of about 500 to about 5,000 psig each, and step (c) includes the step of collecting at least a portion of X in a receptacle that moves proximate the exit end of the chromatographic bed at substantially the same velocity that the feed stream advances with respect to the chromatographic bed.

6. The method of claim 1 wherein the feed stream further comprises chromatographic species Y, step (a) includes the step of introducing the feed stream and the eluent stream at a pressure of about 800 to about 5,000 psig each, and step (c) includes the step of collecting substantially pure X and substantially pure Y in substantially separate receptacles that sequentially move proximate the exit end of the chromatographic bed at substantially the same velocity that the feed stream advances with respect to the chromatographic bed.

7. The method of claim 1 wherein the chromatographic bed is held substantially fixed and the location at which the feed stream is introduced into the bed is sequentially moved with respect to the chromatographic bed.

8. A continuous, high performance liquid chromatographic (HPLC) method comprising the steps of:
   (a) simultaneously introducing a feed mixture stream, a displacer reagent stream, and a barrier reagent stream, at a pressure of at least about 500 psig each, proximate the entrance end of a chromatographic bed, the feed stream comprising chromatographic species X and Y wherein Y has a greater affinity than X for the bed, the displacer stream comprising a species D, and the barrier stream comprises a chromatographic species B wherein B has a lesser affinity than X for the bed;
   (b) moving the streams with respect to the chromatographic bed;

(c) collecting substantially pure X proximate the exit end of the chromatographic bed; and (d) collecting substantially pure Y proximate the exit end of the chromatographic bed.

9. The method of claim 8 wherein step (b) is repeated as many times as necessary so that all portions of the chromatographic bed are sequentially contacted by the feed mixture stream, the displacer reagent stream, and the barrier reagent stream.

10. The method of claim 8 wherein step (a) includes the step of introducing each stream at a pressure of about 500 to about 5,000 psig each.

11. The method of claim 8 wherein step (a) includes the step of introducing each stream at a pressure of about 800 to about 5,000 psig each.

12. The method of claim 8 wherein step (c) includes the step of collecting at least a portion of X in a first receptacle that moves proximate the exit end of the chromatographic bed at substantially the same velocity that the feed mixture stream advances with respect to the chromatographic bed, and step (d) includes the step of collecting at least a portion of Y in a second receptacle that moves proximate the exit end of the chromatographic bed at substantially the same velocity that the feed mixture stream advances with respect to the chromatographic bed.

13. The method of claim 8 wherein step (c) includes the step of collecting X in a first series of receptacles that sequentially move proximate the exit end of the chromatographic bed at substantially the same velocity that the feed stream advances with respect to the chromatographic bed, and step (d) includes the step of collecting Y in a second series of receptacles that sequentially move proximate the exit end of the chromatographic bed at substantially the same velocity that the feed stream advances with respect to the chromatographic bed.

14. The method of claim 8 wherein step (a) includes the step of simultaneously introducing a purge stream, at a pressure of at least about 500 psig, proximate the entrance end of the chromatographic bed.

15. The method of claim 8 wherein D has a greater affinity than Y for the bed.

16. The method of claim 8 wherein D has a greater affinity than the bed for X and Y.

17. The method of claim 8 wherein the chromatographic bed is held substantially fixed and the locations at which the feed mixture stream, the displacer reagent stream, and the barrier reagent stream are introduced into the bed are sequentially moved with respect to the chromatographic bed.

18. The method of claim 8 wherein step (a) includes the step of simultaneously introducing a purge stream, at a pressure of at least about 500 psig, proximate the entrance end of the chromatographic bed, the chromatographic bed is held substantially fixed, and the locations at which the feed mixture stream, the displacer reagent stream, the barrier reagent stream, and the purge stream are introduced into the bed are sequentially moved with respect to the chromatographic bed.

19. The method of claim 8 wherein step (a) includes the step of simultaneously introducing a purge stream, at a pressure of at least about 500 psig, proximate the entrance end of the chromatographic bed, the chromatographic bed is held substantially fixed, and the feed mixture stream, the displacer reagent stream, and the barrier reagent stream are each introduced into the bed by sequentially interrupting different portions of the purge stream flow.

* * * * *